US011590282B2

(12) United States Patent
Loutseiko et al.

(10) Patent No.: US 11,590,282 B2
(45) Date of Patent: Feb. 28, 2023

(54) INSERTION SITE MONITORING METHODS AND RELATED INFUSION DEVICES AND SYSTEMS

(71) Applicant: MEDTRONIC MINIMED, INC., Northridge, CA (US)

(72) Inventors: Mikhail Loutseiko, Granada Hills, CA (US); Anirban Roy, Agoura Hills, CA (US); Benyamin Grosman, Valley Village, CA (US); Di Wu, Montrose, CA (US); Rebecca K. Gottlieb, Culver City, CA (US); Neha J. Parikh, West Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 338 days.

(21) Appl. No.: 17/077,960

(22) Filed: Oct. 22, 2020

(65) Prior Publication Data

US 2021/0038812 A1    Feb. 11, 2021

Related U.S. Application Data

(60) Continuation of application No. 16/297,471, filed on Mar. 8, 2019, now Pat. No. 10,842,936, which is a
(Continued)

(51) Int. Cl.
*A61M 5/172* (2006.01)
*G16H 40/63* (2018.01)
(Continued)

(52) U.S. Cl.
CPC ...... *A61M 5/1723* (2013.01); *A61M 5/14244* (2013.01); *A61M 5/16836* (2013.01);
(Continued)

(58) Field of Classification Search
CPC .......... A61M 2205/52; A61M 5/14244; A61M 5/16836; A61M 5/1723
See application file for complete search history.

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| EP | 2633456 A1 | 9/2013 |
| EP | 2897070 A1 | 7/2015 |
| WO | 2013033025 A1 | 3/2013 |

OTHER PUBLICATIONS

Nihat Baysal, et al: "Detectng Sensor and Insulin Infusion Set Anomalies in an Artificial Pancreas", 2013 American Control Conference (ACC), IEEE, Jun. 17, 2013 (Jun. 17, 2013), pp. 2929-2933, XP032476248, ISSN: 0743-1619, DOI: 10.1109/ACC.2013.6580279.

(Continued)

*Primary Examiner* — Deanna K Hall
(74) *Attorney, Agent, or Firm* — Lorenz & Kopf LLP

(57) ABSTRACT

Infusion systems, infusion devices, and related operating methods are provided. An exemplary method of operating an infusion device involves obtaining one or more measurement values of a physiological condition in the body of a user during an initial monitoring period and determining a fasting reference value for a metric based on the one or more measurement values. After the initial monitoring period, the method continues by obtaining an updated measurement value during a fasting period, determining a current value for the metric based at least in part on the updated measurement value, and generating a notification in response to a deviation between the current value and the fasting reference (Continued)

value exceeding a threshold indicative of insertion site loss or other loss of effectiveness.

20 Claims, 9 Drawing Sheets

Related U.S. Application Data division of application No. 15/389,246, filed on Dec. 22, 2016, now Pat. No. 10,272,201.

(51) Int. Cl.

| | | |
|---|---|---|
| *G16H 20/17* | (2018.01) | |
| *A61M 5/142* | (2006.01) | |
| *A61M 5/168* | (2006.01) | |
| *A61B 5/145* | (2006.01) | |
| *A61B 5/00* | (2006.01) | |

(52) U.S. Cl.
CPC ............ *G16H 20/17* (2018.01); *G16H 40/63* (2018.01); *A61B 5/14532* (2013.01); *A61B 5/4839* (2013.01); *A61M 2005/14208* (2013.01); *A61M 2205/50* (2013.01); *A61M 2205/502* (2013.01); *A61M 2205/52* (2013.01); *A61M 2230/201* (2013.01)

(56) References Cited

U.S. PATENT DOCUMENTS

| | | | |
|---|---|---|---|
| 4,755,173 | A | 7/1988 | Konopka et al. |
| 5,080,653 | A | 1/1992 | Voss et al. |
| 5,097,122 | A | 3/1992 | Colman et al. |
| 5,391,250 | A | 2/1995 | Cheney, II et al. |
| 5,485,408 | A | 1/1996 | Blomquist |
| 5,505,709 | A | 4/1996 | Funderburk et al. |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,088,608 | A | 7/2000 | Schulman et al. |
| 6,119,028 | A | 9/2000 | Schulman et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,485,465 | B2 | 11/2002 | Moberg et al. |
| 6,544,212 | B2 | 4/2003 | Galley et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,589,229 | B1 | 7/2003 | Connelly et al. |
| 6,591,876 | B2 | 7/2003 | Safabash |
| 6,641,533 | B2 | 11/2003 | Causey, III et al. |
| 6,659,980 | B2 | 12/2003 | Moberg et al. |
| 6,736,797 | B1 | 5/2004 | Larsen et al. |
| 6,740,072 | B2 | 5/2004 | Starkweather et al. |
| 6,749,587 | B2 | 6/2004 | Flaherty |
| 6,752,787 | B1 | 6/2004 | Causey, III et al. |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,817,990 | B2 | 11/2004 | Yap et al. |
| 6,827,702 | B2 | 12/2004 | Lebel et al. |
| 6,932,584 | B2 | 8/2005 | Gray et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,323,142 | B2 | 1/2008 | Pendo et al. |
| 7,399,277 | B2 | 7/2008 | Saidara et al. |
| 7,402,153 | B2 | 7/2008 | Steil et al. |
| 7,442,186 | B2 | 10/2008 | Blomquist |
| 7,602,310 | B2 | 10/2009 | Mann et al. |
| 7,621,893 | B2 | 11/2009 | Moberg et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 8,474,332 | B2 | 7/2013 | Bente, IV et al. |
| 8,674,288 | B2 | 3/2014 | Hanson et al. |
| 2003/0028089 | A1 | 2/2003 | Galley et al. |
| 2007/0123819 | A1 | 5/2007 | Mernoe et al. |
| 2010/0160861 | A1 | 6/2010 | Causey, III et al. |
| 2016/0175520 | A1 | 6/2016 | Palerm et al. |
| 2016/0279336 | A1 | 9/2016 | Roy |
| 2017/0049962 | A1 | 2/2017 | Parikh et al. |

OTHER PUBLICATIONS

Marzia Cescon, et al: "Early Detection of Infusion Set Failure During Insulin Pump Therapy in Type 1 Diabetes", Journal of Diabetes Science and Technology, vol. 10, No. 6, Sep. 12, 2016 (Sep. 12, 2016), pp. 1268-1276, XP055442304, US ISSN: 1932-2968, DOI: 10.1177/1932296816663962.

INSERTION SITE MONITORING METHODS AND RELATED INFUSION DEVICES AND SYSTEMS

CROSS-REFERENCE TO RELATED APPLICATIONS

This application is a continuation of U.S. patent application Ser. No. 16/297,471, filed Mar. 8, 2019, which is a division of U.S. patent application Ser. No. 15/389,246, filed Dec. 22, 2016, now issued U.S. Pat. No. 10,272,201.

TECHNICAL FIELD

Embodiments of the subject matter described herein relate generally to medical devices, and more particularly, embodiments of the subject matter relate to detecting insertion site conditions during operation of a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics. Continuous insulin infusion provides greater control of a patient with diabetes glucose levels, and hence, control schemes are being developed that allow insulin infusion pumps to monitor and regulate a user's blood glucose level in a substantially continuous and autonomous manner.

In practice, it is advisable for the infusion set being utilized with the infusion device to be changed or replaced periodically to prevent infection. To mitigate tissue resistance and maintain effectiveness of insulin absorption, it is also advisable to periodically change or vary the location where the infusion set is inserted into the body, also known as the insertion site. Failure to timely change the infusion set or the insertion site can have undesirable physiological consequences, such as a potential hyperglycemic event. Accordingly, patients have typically been instructed to replace infusion sets within a fixed period of time (e.g., every 2 to 3 days) that attempts to ensure preemptive replacement that provides a safety margin in advance of the time of when a particular infusion set at a particular insertion site is likely to lose effectiveness. Preemptively replacing an infusion set can be beneficial for safety purposes, but it may also result in some infusion sets being replaced prematurely when it could otherwise be desirable to maximize the lifetime of the infusion set. For example, patients who are traveling, have a limited supply of infusion sets on hand, do not have immediate access to an infusion set, or experiencing other extenuating circumstances may prefer to avoid having to replace an infusion set according to a fixed schedule.

Additionally, some patients may forget to replace or rotate their infusion set. While providing reminders based on a fixed period of time may be effective, some patients may disregard or ignore the messages based on a perception that the infusion set is still functioning normally. Accordingly, there is a need to prolong the usable lifetime of an infusion set while also ensuring that patients are notified in a timely manner before any adverse events.

BRIEF SUMMARY

Infusion systems, infusion devices, and related operating methods are provided. An embodiment of a method of operating an infusion device to deliver fluid capable of influencing a physiological condition to a body of a user is provided. The method involves obtaining, from a sensing arrangement providing sensed measurements of the physiological condition in the body of the user, one or more measurement values during an initial monitoring period and determining a fasting reference value for a metric based on the one or more measurement values. After the initial monitoring period, the method continues by obtaining, from the sensing arrangement, an updated measurement value during a fasting period, determining a current value for the metric based at least in part on the updated measurement value, and generating a notification in response to a deviation between the current value and the fasting reference value exceeding a threshold.

Another embodiment of operating an infusion device operable to deliver insulin to a body of a patient involves obtaining, from a sensing arrangement, sensed glucose measurement values of a glucose level in the body of the patient during fasting periods during an initial period after initialization of an infusion set associated with the infusion device, determining a fasting amount of insulin in the body of the patient during the fasting periods, and determining a reference insulin estimate for achieving a reference glucose value based at least in part on the fasting amount of insulin and the sensed glucose measurement values. After the initial period, the method continues by obtaining, from the sensing arrangement, an updated glucose measurement value during a subsequent fasting period, determining a current amount of insulin in the body of the patient, determining a current insulin estimate for achieving the reference glucose value based at least in part on the current amount of insulin and the updated glucose measurement value, and generating an insertion site notification based on a relationship between the current insulin estimate and the reference insulin estimate.

In another embodiment, an apparatus of an infusion device is provided. The infusion device includes a communications interface to receive sensed measurements of a physiological condition in a body of a user, a fluid interface providing fluid communication with an infusion set to deliver fluid influencing the physiological condition to the body of the user, a user interface, and a control module coupled to the communications interface and the user interface. The control module is configurable to obtain one or more fasting measurement values for the physiological condition from the sensed measurements corresponding to fasting periods during an initial period of a lifetime of the infusion set, determine a fasting reference value for a metric based on the one or more fasting measurement values, and after the initial period, obtain an updated measurement value from the sensed measurements corresponding to a subsequent fasting period, determine a current value for the metric based at least in part on the updated measurement value, and provide a notification via the user interface based on a difference between the current value and the fasting reference value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
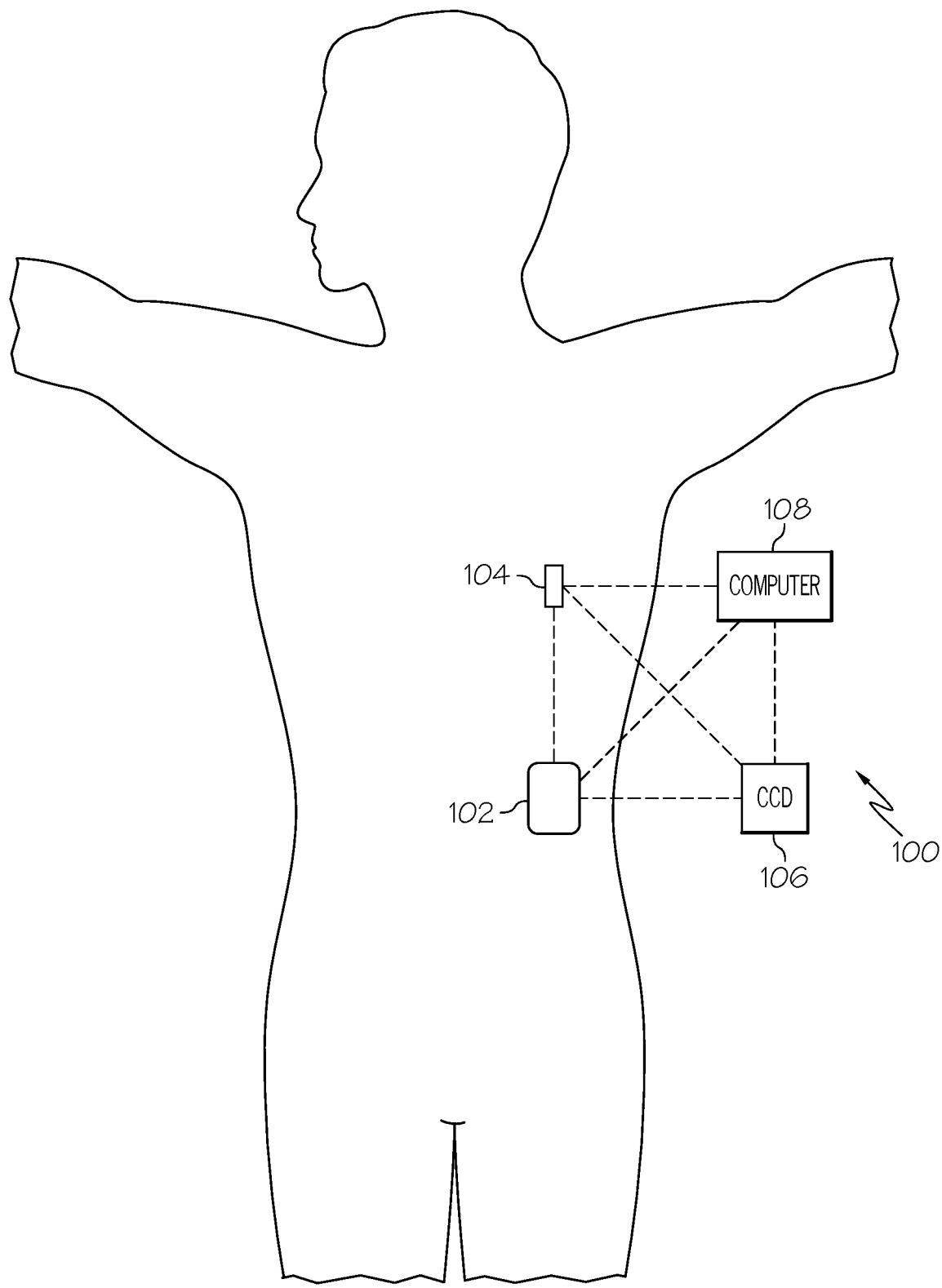
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097, 122; 6,485,465; 6,554,798; 6,558,320; 6,558,351; 6,641, 533; 6,659,980; 6,752,787; 6,817,990; 6,932,584; and 7,621,893; each of which are herein incorporated by reference.

Embodiments of the subject matter described herein generally relate to infusion systems including a fluid infusion device having a motor or other actuation arrangement that is operable to linearly displace a plunger (or stopper) of a reservoir provided within the fluid infusion device to deliver a dosage of fluid, such as insulin, to the body of a patient (or user). Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below, primarily in the context of FIGS. 8-9, in exemplary embodiments described herein, the infusion device monitors sensed glucose measurement values for changes in a patient's fasting glucose levels over the lifetime of an infusion set and generates an alert or notification when the magnitude of the change in fasting glucose levels indicates that the infusion set should be replaced, inspected, rotated, or otherwise attended to. In this regard, as the effectiveness of the current infusion set or the current insertion site wanes (e.g., due to increasing tissue resistance or decreased absorption), fasting glucose values trend upward in correlation with the lifetime of the infusion set. Accordingly, changes in the patient's fasting glucose levels can be utilized to detect insertion site loss or other potential problems associated with the infusion set or insertion site. By providing a timely notification to change an infusion set when a patient's daily glucose profile or fasting glucose levels drifts towards higher glucose values, potential hyperglycemic events can be avoided. At the same time, by virtue of the monitoring of fasting glucose levels, infusion sets do not need to be preemptively replaced, which, in turn may allow for the usable life of the infusion set to be increased beyond a fixed replacement schedule.

In exemplary embodiments, during an initial monitoring period after an infusion set is initialized or changed, the infusion device obtains sensed glucose measurement values that are coincident with, contemporaneous to, or otherwise temporally correspond to any fasting periods within the initial monitoring period and determines a fasting value for a reference metric based on those fasting measurement values corresponding to fasting periods. Depending on the embodiment, the fasting reference value may be an average fasting glucose measurement value over the fasting periods within the initial monitoring period, an estimated amount of insulin needed for achieving a target glucose value based on the fasting glucose measurement values, or some other metric that is a function of the glucose measurement values corresponding to the fasting periods within the initial monitoring period.

After the initial monitoring period, the sensed glucose measurement values obtained by the infusion device during subsequent fasting periods are utilized to determine an updated (or current) fasting value for the reference metric based on those recently sensed glucose measurement values that are coincident with, contemporaneous to, or otherwise temporally correspond to a subsequent fasting period. The current fasting value for the reference metric is compared to the fasting reference value determined based on the fasting sensor data from the initial monitoring period, and in response to a deviation between the current fasting value and the fasting reference value that exceeds a threshold, a notification is generated that indicates that the patient needs to replace, rotate, inspect, or otherwise attend to the infusion set.

It should be noted that although the subject matter may be described herein primarily in the context of the infusion device receiving and monitoring measurement values, the subject matter is not necessarily limited to implementation by the infusion device. In practice, the subject matter may be implemented in an equivalent manner by any other electronic or computing device that is communicatively coupled to at least one of the sensing arrangement and the infusion device and capable of receiving sensed measurement values for the patient as described below.

Infusion System Overview

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological or physiological condition of the user, such as a blood glucose level, or the like, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In various embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In one or more exemplary embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
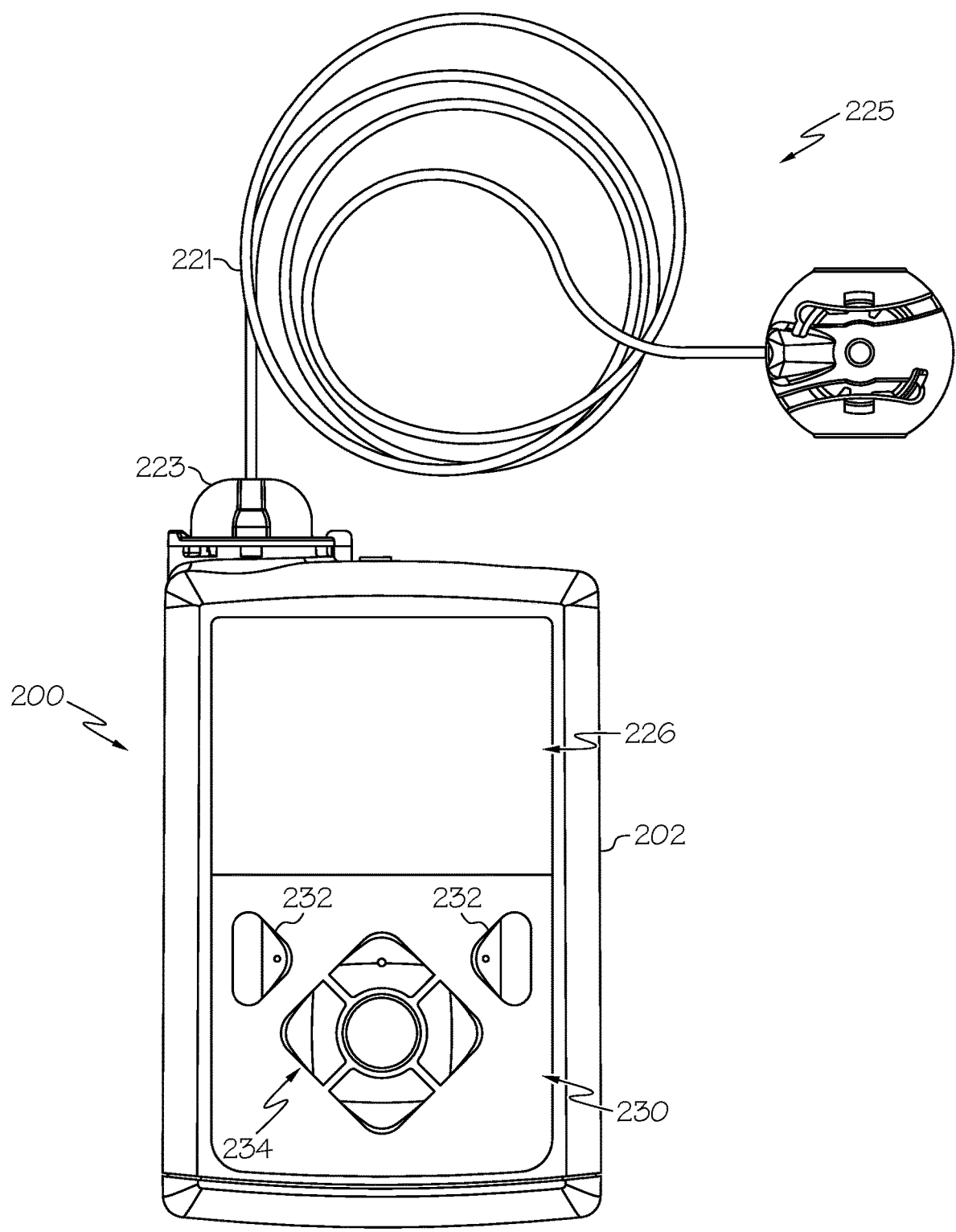
FIG. 2 depicts a plan view of an exemplary embodiment of a fluid infusion device suitable for use in the infusion system of FIG. 1.
Figure 3:
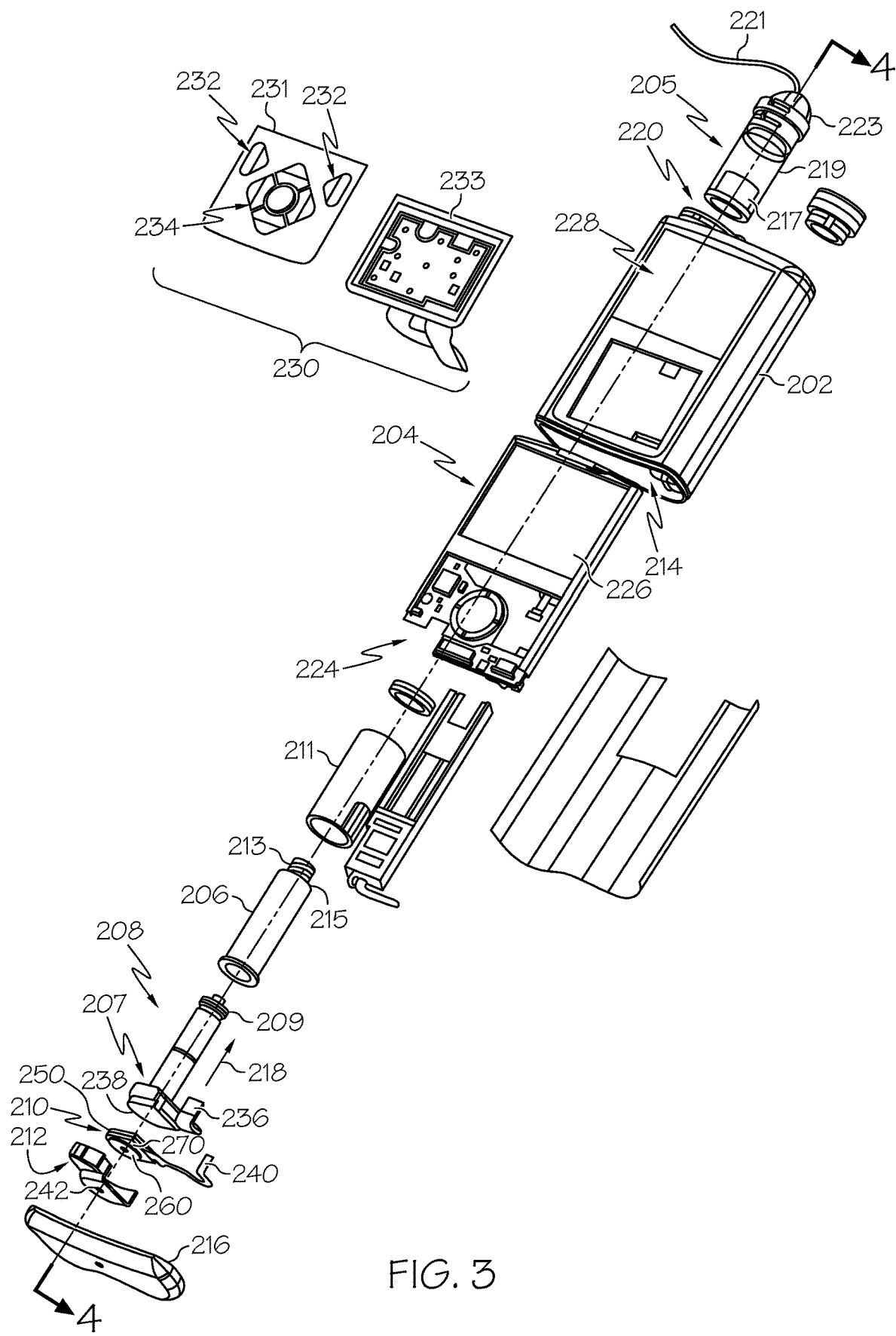
FIG. 3 is an exploded perspective view of the fluid infusion device of FIG. 2.
Figure 4:
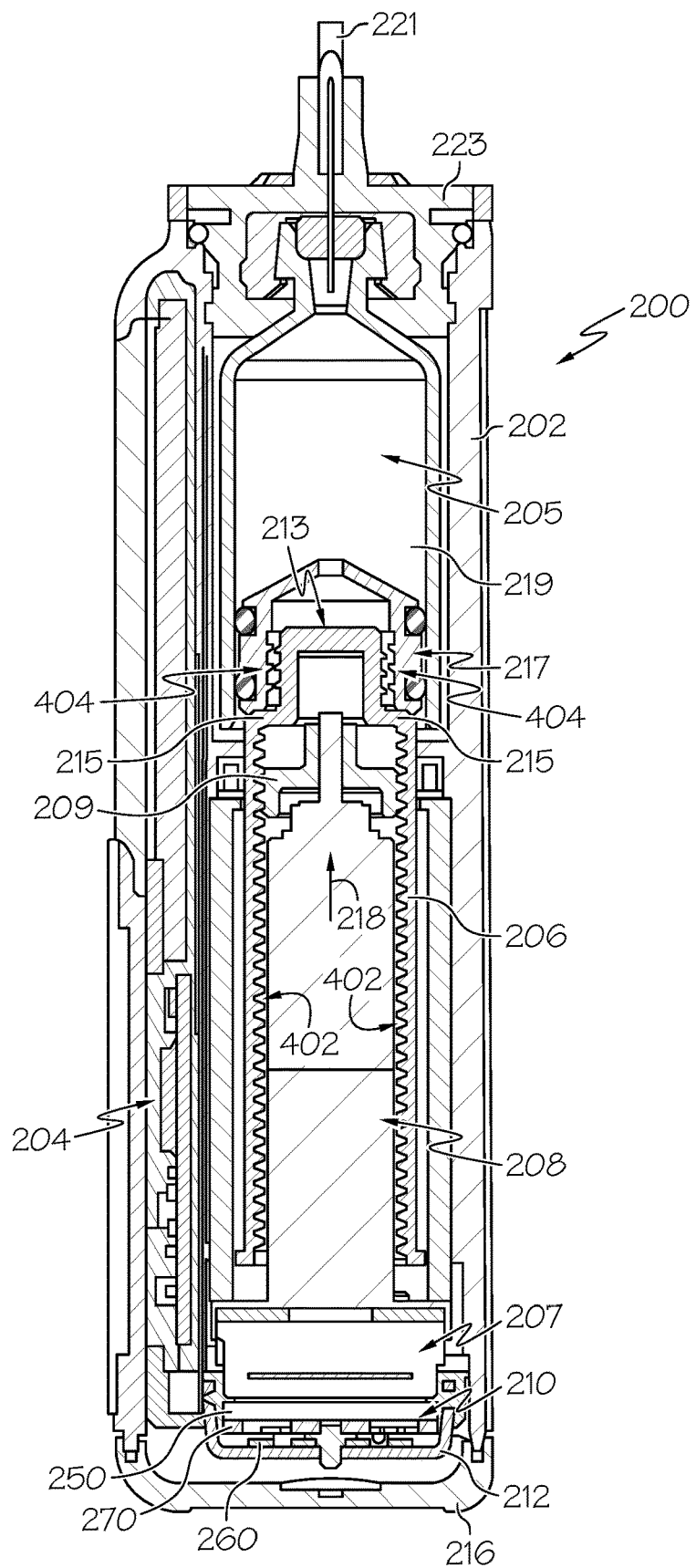
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
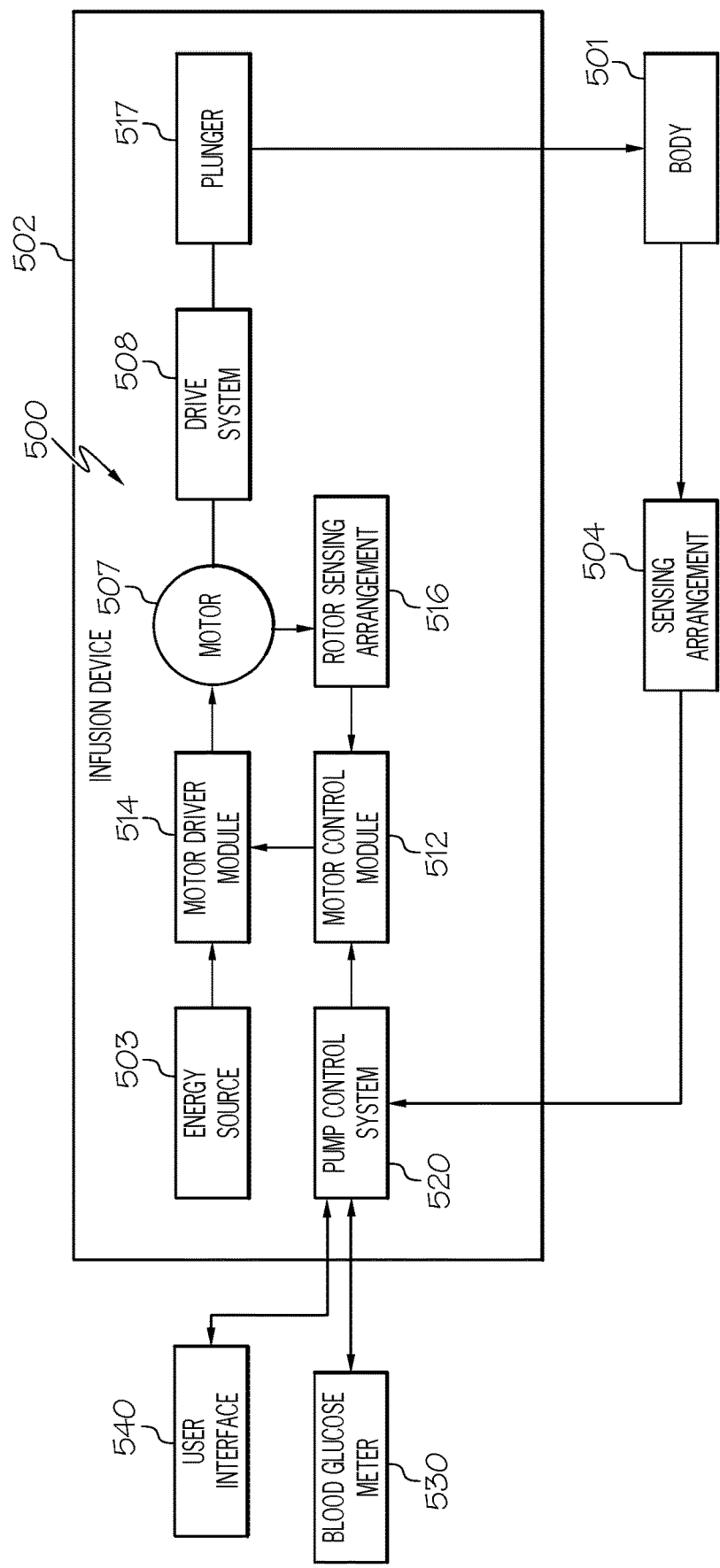
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is capable of controlling or otherwise regulating a physiological condition in the body 501 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, a blood glucose value calculated based on the electrical signals output by the sensing element(s) of the sensing arrangement 504 may alternatively be referred to herein as the sensor glucose value, the sensed glucose value, or variants thereof.

In the illustrated embodiment, the pump control system 520 generally represents the electronics and other components of the infusion device 502 that control operation of the fluid infusion device 502 according to a desired infusion delivery program in a manner that is influenced by the sensed glucose value indicative of a current glucose level in the body 501 of the user. For example, to support a closed-loop operating mode, the pump control system 520 maintains, receives, or otherwise obtains a target or commanded glucose value, and automatically generates or otherwise determines dosage commands for operating an actuation arrangement, such as a motor 507, to displace the plunger 517 (e.g., via a drive system 508) and deliver insulin to the body 501 of the user based on the difference between a sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), and/or other glucose threshold value(s) in a data storage element accessible to the pump control system 520.

The target glucose value and other threshold glucose values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the CCD 106 or the computing device 108.

Figure 6:
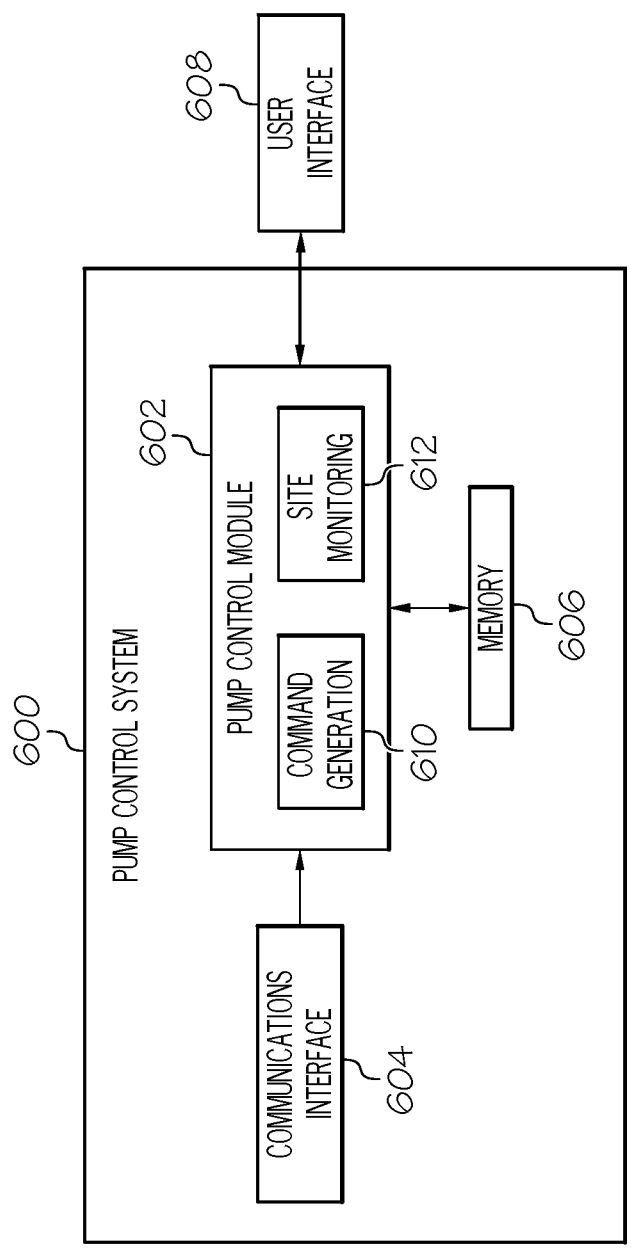
FIG. 6 is a block diagram of an exemplary pump control system suitable for use in the control system of FIG. 5.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In exemplary embodiments, the pump control module 602 is also coupled to one or more user interface elements 608 (e.g., user interface 230, 540) for receiving user input and providing notifications, alerts, or other therapy information to the user. Although FIG. 6 depicts the user interface element 608 as being separate from the pump control system 600, in various alternative embodiments, the user interface element 608 may be integrated with the pump control system 600 (e.g., as part of the infusion device 200, 502), the sensing arrangement 504 or another element of an infusion system 100 (e.g., the computer 108 or CCD 106).

Referring to FIG. 6 and with reference to FIG. 5, the communications interface 604 generally represents the hardware, circuitry, logic, firmware and/or other components of the pump control system 600 that are coupled to the pump control module 602 and configured to support communications between the pump control system 600 and the sensing arrangement 504. In this regard, the communications interface 604 may include or otherwise be coupled to one or more transceiver modules capable of supporting wireless communications between the pump control system 520, 600 and the sensing arrangement 504 or another electronic device 106, 108 in an infusion system 100. In other embodiments, the communications interface 604 may be configured to support wired communications to/from the sensing arrangement 504.

The pump control module 602 generally represents the hardware, circuitry, logic, firmware and/or other component of the pump control system 600 that is coupled to the communications interface 604 and configured to determine dosage commands for operating the motor 506 to deliver fluid to the body 501 based on data received from the sensing arrangement 504 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 506 of the infusion device 502 in an autonomous operating mode based at least in part on a current measurement value for a condition in the body 501 of the user. Additionally, in exemplary embodiments described herein, the pump control module 602 also implements or otherwise executes an insertion site monitoring application 612 that supports monitoring sensed glucose measurement values received via the sensing arrangement 504, analyzing the efficacy of the current infusion set or current insertion site based on the sensed glucose measurement values, and generating user notifications or alerts provided to the patient or user via the user interface element 608, as described in greater detail below in the context of FIGS. 8-9.

Still referring to FIG. 6, in a closed-loop operating mode, the command generation application 610 may determine a dosage command for operating the motor 506 to deliver insulin to the body 501 of the user based at least in part on the current glucose measurement value most recently received from the sensing arrangement 504 to regulate the user's blood glucose level to a target reference glucose value. Additionally, the command generation application 610 may generate dosage commands for boluses that are manually-initiated or otherwise instructed by a user via a user interface element 608. For example, regardless of the operating mode being implemented, the command generation application 610 may determine a dosage command for operating the motor 506 to deliver a bolus of insulin to the body 501 of the user that corresponds to a correction bolus or meal bolus amount selected or otherwise indicated by the user via the user interface element 230, 540, 608.

Depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the applications 610, 612 and perform the tasks, operations, functions, and processes described in greater detail below.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
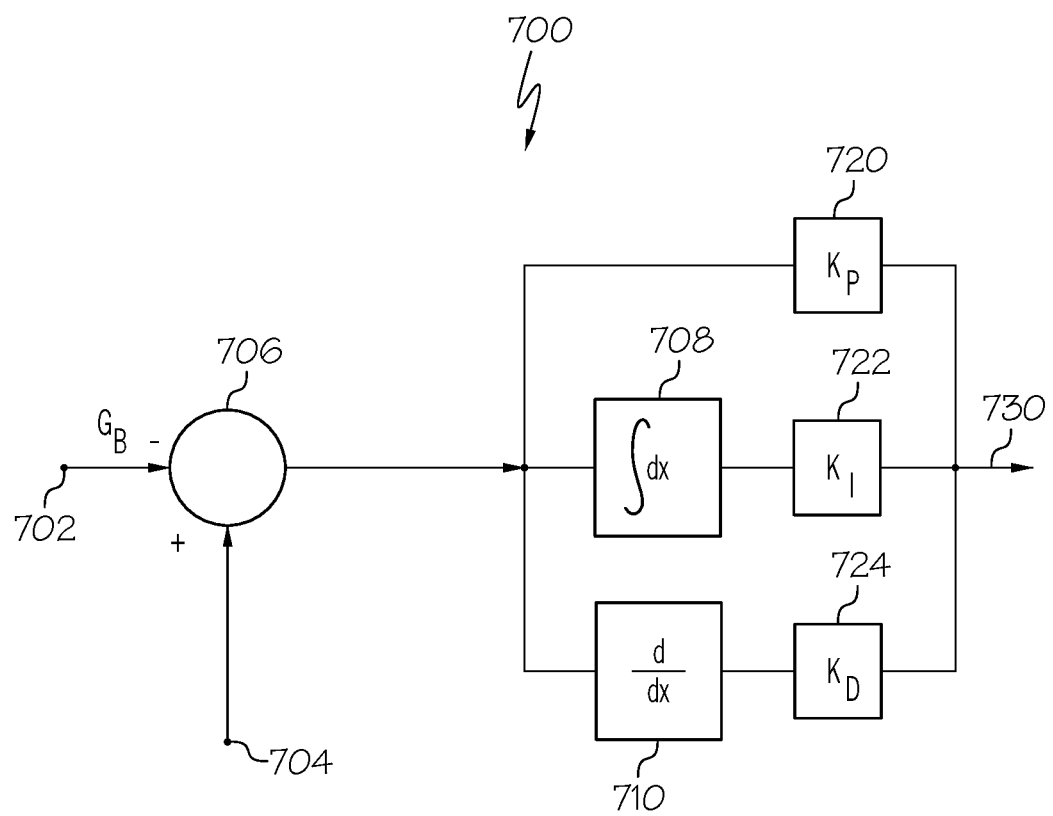
FIG. 7 is a block diagram of a closed-loop control system that may be implemented or otherwise supported by the pump control system in the fluid infusion device of FIG. 5 in one or more exemplary embodiments.

FIG. 7 depicts an exemplary closed-loop control system 700 that may be implemented by a pump control system 520, 600 to provide a closed-loop operating mode that autonomously regulates a condition in the body of a user to a reference (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be dynamically calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 510 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 510 to deliver insulin to the body of the user to influence the user's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determine gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

Insertion Site Loss Detection

As described above, in exemplary embodiments described herein, measurement values from a sensing arrangement 104, 504 are utilized to determine whether an insertion site loss has occurred and provide corresponding notifications regarding use of the current infusion set and/or the current insertion site. In this regard, insertion site loss should be understood as referring to a condition where sensed glucose measurement values indicate the effectiveness of the current configuration of infusion set and insertion site has decreased to the point that a new infusion set and/or new insertion site should be utilized to avoid potential adverse events. For example, in response to detecting an insertion site loss condition, an infusion device 102, 502 may generate an alert that indicates that the infusion set 225 should be replaced and rotated to a new insertion site.

It should be noted that insertion site notifications may be provided using any number of devices of an infusion system 100, 500. For example, one or more graphical user interface (GUI) notifications may be generated or provided on any one of the infusion device 102, 200, 502 (e.g., display element 226, user interface element 540, 608, or the like), the sensing arrangement 104, 504, the computer 106, and/or the CCD 108. That said, for purposes of explanation, the subject matter may be described herein primarily in the context of the pump control system 520, 600 of the infusion device 102, 200, 502 generating the insertion site notifications; however, it should be appreciated that various aspects of the processes described below in the context of FIGS. 8-9 could be implemented or supported by any number of the other electronic devices in an infusion system 100, 500, and the subject matter described herein is not necessarily limited to implementation by an infusion device 102, 200, 502.

Figure 8:
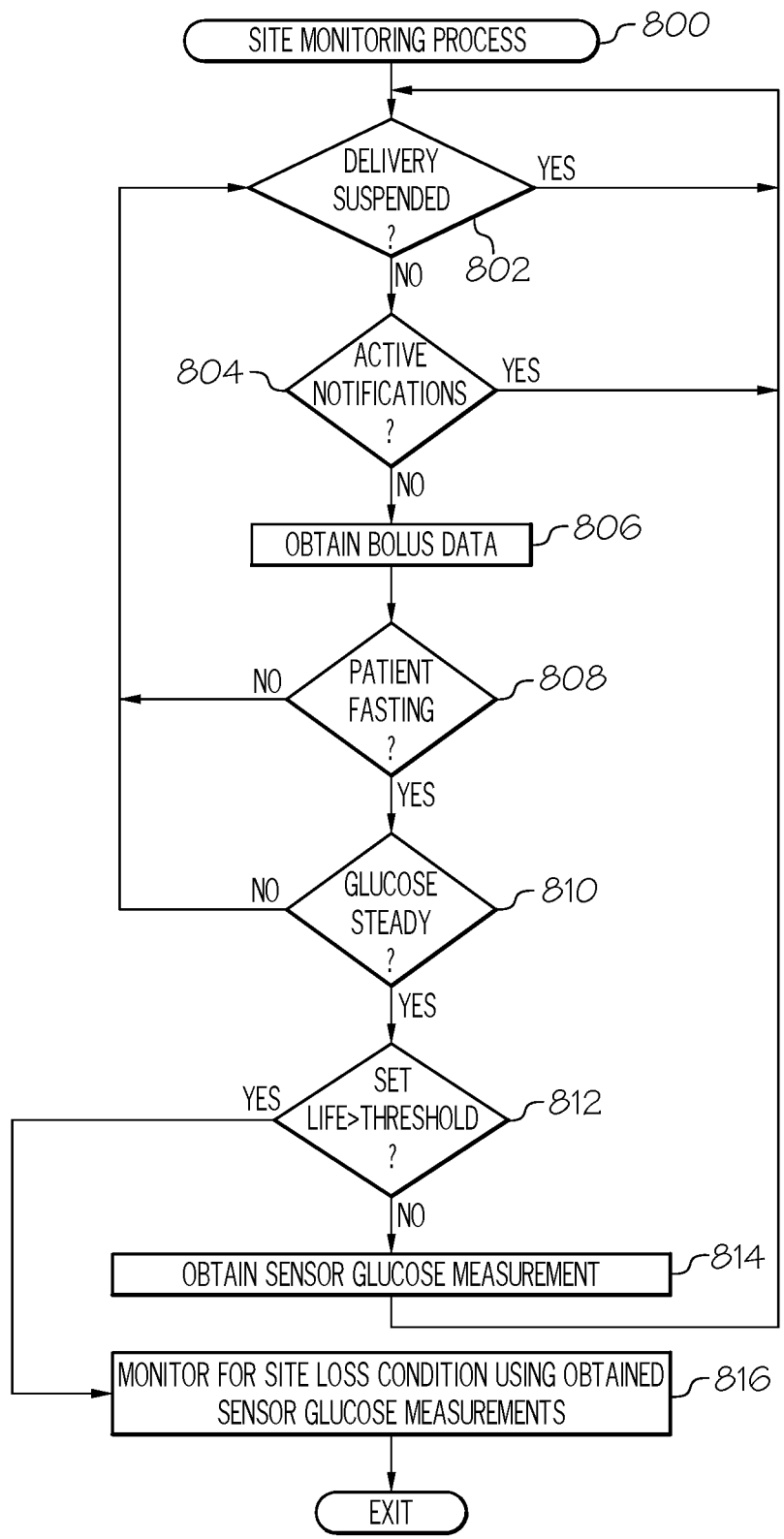
FIG. 8 is a flow diagram of an exemplary site monitoring process suitable for use with the control system of FIG. 5 in one or more exemplary embodiments.

FIG. 8 depicts an exemplary site monitoring process 800 suitable for implementation by a control system associated with an electronic device, such as a control system 520, 600 in an infusion device 102, 200, 502, to establish a fasting reference value for use in detecting an insertion site loss condition, as described in greater detail below in the context of FIG. 9. The various tasks performed in connection with the site monitoring process 800 may be performed by hardware, firmware, software executed by processing circuitry, or any combination thereof. For illustrative purposes, the following description refers to elements mentioned above in connection with FIGS. 1-7. In practice, portions of the site monitoring process 800 may be performed by different elements of an infusion system, however, for purposes of explanation, the site monitoring process 800 may be described herein primarily in the context of the infusion device 502, the pump control system 520, 600, and/or the pump control module 602. It should be appreciated that the site monitoring process 800 may include any number of additional or alternative tasks, the tasks need not be performed in the illustrated order and/or the tasks may be performed concurrently, and/or the site monitoring process 800 may be incorporated into a more comprehensive procedure or process having additional functionality not described in detail herein. Moreover, one or more of the tasks shown and described in the context of FIG. 8 could be omitted from a practical embodiment of the site monitoring process 800 as long as the intended overall functionality remains intact.

In exemplary embodiments, the site monitoring process 800 is performed whenever a new infusion set is initialized and inserted in the body of a patient at an insertion site. The site monitoring process 800 monitors sensed measurement values during an initial monitoring period corresponding to an initial phase of the lifetime of the infusion set (e.g., the first 48 hours or the like), detects or identifies fasting conditions during that initial monitoring period, and then determines a fasting reference value for the infusion set based on the sensed measurement values coincident with, concurrent to, or otherwise temporally corresponding to fasting periods during the initial monitoring period. As described in greater detail below, a fasting period should be understood as referring to a window of time during which a fasting condition exists and the sensed glucose measurement values are relatively steady and not overly susceptible to variations due to insulin that remains active in the body of the patient.

The site monitoring process 800 detects or otherwise identifies a fasting condition by verifying or otherwise identifying when delivery of fluid by an infusion device is not currently suspended, when there are no active alerts or notification, and when a meal or bolus has not occurred within a threshold period of time (tasks 802, 804, 806, 808). In this regard, the monitoring application 612 may interact with one or more of the command generation application 610, the memory 606, and/or another application or process executed by the pump control module 602 to obtain information or data characterizing current delivery status and verify that the delivery of fluid is not currently suspended. For example, the monitoring application 612 may monitor a flag bit having a value that is set by the command generation application 610 to indicate whether the delivery is enabled (e.g., a logical low or '0' bit value) or suspended (e.g., a logical high or '1' bit value). After verifying delivery is not suspended, the monitoring application 612 may similarly interact with one or more of the command generation application 610, the memory 606, and/or another application or process executed by the pump control module 602 to obtain information or data characterizing current user interface status and verify that there is not an active alert or user notification presented by a user interface element 608.

After verifying delivery is not suspended and that there are no active alerts, the monitoring application 612 obtains historical bolus data from memory 606, which includes information or data characterizing the timing of boluses previously delivered by the infusion device 502 or meals manually announced, entered or otherwise input to the infusion device 502 by the patient or another user. In some embodiments, meals may also be automatically detected by the pump control module 602 based on sensed measurement values or other data. Based on the historical bolus and meal data, the monitoring application 612 verifies that the patient has not consumed a meal or administered a bolus within a threshold period of time (e.g., within the preceding 5 hours), and therefore, is likely to be fasting.

In exemplary embodiments, the site monitoring process 800 also verifies or otherwise confirms the physiological condition in the body of the patient is substantially constant or steady before detecting or identifying a fasting period for determining a fasting reference value (task 810). In this regard, the monitoring application 612 may verify or otherwise confirm that variations in the sensed measurement values over a preceding time interval are within a threshold range. For example, in one embodiment, the monitoring application 612 verifies that variations in sensed glucose measurement values over the preceding two hours of time is less than 20 milligrams per deciliter (mg/dL). Additionally, in exemplary embodiments, the monitoring application 612 also calculates or otherwise determines an estimated plasma insulin in the body of the patient and verifies or otherwise confirms the plasma insulin rate of change is less than a threshold value. In this regard, the monitoring application 612 ensures any lingering active insulin in the body of the patient is not unduly influencing sensed glucose measurement values during the fasting period. As used herein, the estimated plasma insulin should be understood as referring to an estimation of the concentration of the total insulin present in a patient's blood (including both basal and bolus insulin delivered) and the estimated plasma insulin rate of change corresponds to the rate of change of the total insulin concentration in the patient's blood. Here, it should also be noted that in practical embodiments, the equations utilized to estimate plasma insulin may vary depending on the type(s) of insulin being utilized to account for the rate or speed at which the insulin acts.

In one embodiment, the monitoring application 612 calculates or otherwise determines an estimated plasma insulin using the equation:

$$Ip(s) = \frac{Id(s)}{(50s+1)(70s+1)},$$

where s is the Laplace transform variable, Id(s) is the insulin delivered in units per hour (U/h), and Ip(s) is the estimated plasma insulin in units per hour. In this regard, the estimated plasma insulin rate of change corresponds to the derivative of the estimated plasma insulin equation. In one or more exemplary embodiments, the monitoring application 612 obtains historical delivery data from the command generation application 610 and/or the memory 606 which indicates the respective timing and amounts of insulin delivered by the infusion device 102, 502 over a preceding period of time, and then calculates or otherwise determines the rate of insulin delivered (Id(s)) in units per hour at discrete instances over a preceding duration of time (e.g., the preceding two hours) based on the historical delivery data. Using the insulin delivered, the monitoring application 612 calculates or otherwise determines the estimated plasma insulin (Ip(s)) at discrete instances over the preceding duration of time, and then determines the estimated plasma insulin rate of change between discrete estimated plasma insulin values over the preceding duration of time, and verifies that the difference between the minimum and maximum estimated plasma insulin rate of change values for that preceding duration is less than a threshold value. In this regard, a difference between minimum and maximum estimated plasma insulin rate of change values that exceeds the threshold value indicates that the sensed glucose measurement values are susceptible to variations due to the plasma insulin in the body of the user.

In one or more embodiments, the threshold value for the estimated plasma insulin rate of change is calculated as a function of the patient's total daily insulin requirement. For example, in one embodiments, the monitoring application 612 verifies the deviation in the between the minimum and maximum estimated plasma insulin rate of change values over the preceding two hours is less than a threshold value calculated using the following equation:

$$\frac{TDI}{480},$$

where TDI is the patient's total daily insulin requirement. The patient's total daily insulin requirement may also be calculated or determined by the monitoring application 612 based on historical insulin delivery data, such as, for example, the mean or median amount of insulin delivered per 24-hour time window over a preceding interval (e.g., the median amount of insulin per 24 hours during the preceding week). In other embodiments, the patient's total daily insulin requirement could be input or otherwise provided by a user. In other embodiments, the threshold value is calculated as a function of the patient's basal infusion rate. For example, in one embodiment, the monitoring application 612 verifies the deviation in the between the minimum and maximum estimated plasma insulin rate of change values over the preceding two hours is less than ten percent of the patient's basal rate. In yet other embodiments, the threshold value may be calculated as a function of another reference infusion rate for the patient (e.g., a minimum or maximum infusion rate limit associated with a particular operating mode).

When variations in the measurement values for the physiological condition in the body of the patient as well as variations in other metric(s) characterizing the physiological condition in the body of the patient are less than applicable thresholds or otherwise within an acceptable range, the site monitoring process 800 detects or otherwise identifies a fasting period suitable for determining a fasting value for a reference metric. Thereafter, whenever the patient consumes a meal, delivery is suspended, an alert is generated, or the patient's glucose level or metrics thereof become variable, the site monitoring process 800 determines the current fasting period is over and reverts to monitoring for another fasting period.

Still referring to FIG. 8, after detecting a fasting period, the site monitoring process 800 proceeds with obtaining sensed measurement values corresponding to the fasting period until the lifetime of the infusion set exceeds a threshold lifetime (tasks 812, 814). In this regard, the loop defined by tasks 802, 804, 806, 808, 810, 812, and 814 repeats throughout the initial portion of an infusion set's lifetime to obtain fasting sensed measurement values corresponding to the current configuration of infusion set and insertion site that may be utilized to determine a corresponding fasting reference value and subsequently detect a site loss condition once the lifetime of the infusion set extends beyond a certain duration. For example, in one embodiment, the fasting reference value(s) are determined based on sensed measurement values obtained during fasting periods within the first forty-eight hours after a new infusion set is initialized. In this regard, the monitoring application 612 may implement and initiate a timer upon a new infusion set being initialized or utilized. In one or more embodiments, the monitoring application 612 stores or otherwise maintains sensed glucose measurement values obtained from the sensing arrangement 104, 504 during fasting periods in memory 606 until the lifetime of the infusion set exceeds a threshold duration.

After detecting a fasting period, when the site monitoring process 800 determines the lifetime of the infusion set exceeds a threshold lifetime, the site monitoring process 800 continues by monitoring for a site loss condition using the sensed measurement values obtained for the fasting period(s) during the initial portion of the infusion set's lifetime (task 816). In this regard, the monitoring application 612 calculates or otherwise determines one or more fasting reference values based on the obtained sensed measurement values corresponding to the fasting period(s) during the initial period of the infusion set's lifetime. As described in greater detail below in the context of the site loss detection process 900 of FIG. 9, the monitoring application 612 detects or otherwise identifies a site loss condition when an updated reference value calculated based on obtained sensed measurement values during a current fasting period deviates from a fasting reference value by more than a threshold amount.

Figure 9:
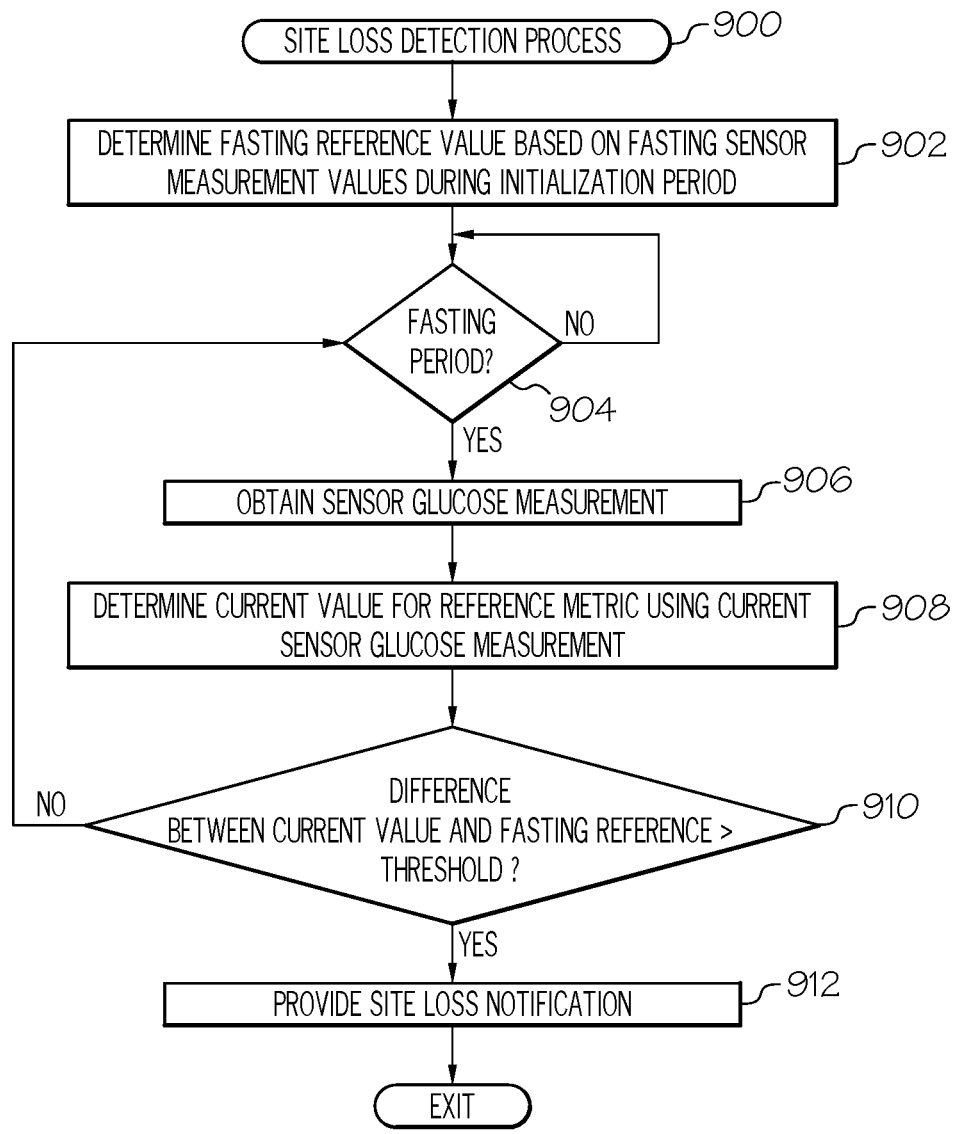
FIG. 9 is a flow diagram of an exemplary site loss detection process suitable for use with the control system of FIG. 5 in conjunction with the site monitoring process of FIG. 8 in one or more exemplary embodiments.

FIG. 9 depicts an exemplary site loss detection process 900 suitable for implementation in conjunction with the site monitoring process 800 of FIG. 8 to detect a site loss condition using a fasting reference value determined based on sensed measurement values obtained during an initial phase of an infusion set's lifetime. The various tasks performed in connection with the site loss detection process 900 may be performed by hardware, firmware, software executed by processing circuitry, or any combination thereof. For illustrative purposes, the following description refers to elements mentioned above in connection with FIGS. 1-7. In practice, portions of the site loss detection process 900 may be performed by different elements of an infusion system, however, for purposes of explanation, the site loss detection process 900 may be described herein primarily in the context of the infusion device 502, the pump control system 520, 600, and/or the pump control module 602. It should be appreciated that the site loss detection process 900 may include any number of additional or alternative tasks, the tasks need not be performed in the illustrated order and/or the tasks may be performed concurrently, and/or the site loss detection process 900 may be incorporated into a more comprehensive procedure or process having additional functionality not described in detail herein. Moreover, one or more of the tasks shown and described in the context of FIG. 9 could be omitted from a practical embodiment of the site loss detection process 900 as long as the intended overall functionality remains intact.

In exemplary embodiments, the site loss detection process 900 is performed once the lifetime of the current infusion set is greater than an initialization period over which reference fasting sensed measurement values are obtained (e.g., task 816). For example, in one or more embodiments, the site loss detection process 900 is performed once the lifetime of an infusion set is greater than forty-eight hours. The site loss detection process 900 calculates or otherwise determines one or more fasting reference measurement values based on sensed measurement values obtained during fasting periods within the initialization period of the infusion set (task 902). For example, in one embodiment, the monitoring application 612 calculates an average fasting sensor glucose level for the patient by averaging the sensed glucose measurement values obtained from the sensing arrangement 104, 504 during the fasting period(s) (e.g., task 814) that occurred during the initial forty-eight hours of the infusion set's usage (e.g., task 812).

In another embodiment, the monitoring application 612 calculates an estimated amount of insulin needed to achieve a target blood glucose level from the patient's fasting blood glucose level. In practice, the target blood glucose level may be a limit associated with an autonomous operating mode supported by the infusion device 102, 502, and in some embodiments, may be patient-specific. For example, in one embodiment, the target blood glucose level may be an upper glucose limit associated with a closed-loop operating mode. In another embodiment, the target blood glucose level may be the same target or reference glucose value associated with the closed-loop operating mode. The estimated amount of insulin needed to achieve a target blood glucose level may be calculated using the equation:

$$Ip(t) + \frac{FBG_T - FBG}{-5400/TDI},$$

where FBG is the fasting sensor glucose level, FBGT is the target blood glucose level, TDI is the patient's total daily insulin requirement, and Ip(t) is the estimated plasma insulin as described above. Thus, in one embodiment, to determine a reference estimated amount of insulin during fasting periods, the monitoring application 612 calculates or otherwise determines estimated plasma insulin values for the fasting period(s) during the initialization period and calculates the reference estimated amount of insulin as a function of the average estimated fasting plasma insulin values during the initialization period and the average fasting sensor glucose level during the initialization period. In some embodiments, the reference estimated amount of insulin at fasting may be calculated or otherwise determined substantially in real-time during the initialization period and dynamically updated on a rolling basis to obtain a moving average over the initialization period having a final value that corresponds to the fasting reference value.

After determining a fasting reference value, the site loss detection process 900 continues by identifying or otherwise determining when a fasting period exists, and in response to detecting a fasting period, obtains a current sensed measurement value, calculates or otherwise determines an updated (or current) value for the reference metric based on the current sensed measurement value, and then detects or identifies a site loss condition based on the difference between the updated reference metric value and the fasting reference value (tasks 904, 906, 908, 910). In a similar manner as described above in the context of FIG. 8, the monitoring application 612 identifies a fasting period when delivery is not suspended (e.g., task 802), there are no active alerts or notifications (e.g., task 804), there are no meals or boluses within a preceding period of time (e.g., tasks 806, 808), and the patient's glucose level is stable (e.g., task 810). When a fasting period exists, the monitoring application 612 obtains the current or most recent sensed glucose measurement value from the sensing arrangement 104, 504, and then calculates a current value for the reference metric substantially in real-time using the current sensed glucose measurement value. In this regard, when the reference metric is an estimated amount of insulin needed to achieve a target blood glucose level, the monitoring application 612 calculates or otherwise determines a current estimated amount of insulin needed to achieve the target blood glucose level from the current glucose level as a function of the current sensed glucose measurement value and the current estimated plasma insulin level using the equations described above.

In exemplary embodiments, the monitoring application 612 detects or otherwise identifies a site loss condition when the difference between the fasting reference value and the current or updated value for the reference metric deviates from the fasting reference value by more than a threshold percentage. For example, in one embodiment, the monitoring application 612 detects a site loss condition when the updated reference metric value is more than thirty percent greater than the fasting reference value. In such embodiments, if the current estimated amount of insulin needed to achieve the target blood glucose level is greater than the fasting reference estimated amount of insulin by more than thirty percent, a site loss condition is detected. Similarly, in embodiments where the glucose level is utilized as the reference metric, a site loss condition may be detected if the current sensed glucose measurement value is greater than the average of the sensed glucose measurement values from the fasting period(s) during the initialization period by more than thirty percent.

Still referring to FIG. 9, in response to detecting a site loss condition, the site loss detection process 900 generates or otherwise provides a user notification or alert that indicates a site loss condition (task 912). In exemplary embodiments, the monitoring application 612 generates or otherwise provides a notification, via the user interface 608, that indicates that the patient needs to change the infusion set, inspect the infusion set (or insertion thereof) for potential malfunction, change the insertion site, and/or the like. In this regard, in some embodiments, the monitoring application 612 may analyze historic delivery data, measurement data, historical insertion site location information, and/or other historical information to provide guidance as to the cause of the notification. For example, based on the current lifetime of the current infusion set relative to preceding infusion sets, the frequency or rate at which the current insertion site is utilized by the patient, and potentially other metrics that may be calculated using historic data, the monitoring application 612 may be able to determine or otherwise assign a likelihood or probability to the potential causes of the site loss notification and provide corresponding guidance to the patient (e.g., by listing replacing the infusion set, inspecting the infusion set, changing the insertion site, and the like in order of likelihood).

In one or more exemplary embodiments, the site loss detection process 900 is persistently performed once the lifetime of an infusion set exceeds a threshold amount. In this regard, while an initial insertion site loss notification may be cleared by a patient after inspecting the insertion site, the site loss detection process 900 may generate additional site loss notifications during subsequent fasting periods to provide continual reminders to the patient throughout the lifetime of the infusion set. Thus, if the patient chooses not to replace the infusion set initially, the patient may be subsequently apprised of the fact that the action taken in response to a preceding notification was not effective at resolving the discrepancy between the current reference metric values and the fasting reference value from the initialization period. Accordingly, the likelihood of the patient utilizing the infusion set for a prolonged duration or other potential adverse events is reduced.

By virtue of the subject matter described herein, a more flexible replacement schedule for infusion sets (and corresponding insertion site rotation) may be adopted, thereby allowing infusion sets to be used for a longer duration rather than replace preemptively. At the same time, infusion sets requiring relatively early replacement may also be alerted when a site loss condition is detected rather than waiting for a fixed time period to elapse after insertion. Site loss notifications may also reduce or eliminate the need for patients to monitor or track the lifetime of the current infusion set, thereby reducing the burden on patients and improving the user experience without compromising patient outcomes.

For the sake of brevity, conventional techniques related to glucose sensing and/or monitoring, closed-loop glucose control, sensor calibration, electrical signals and related processing, user interfaces, alerting, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating a medical device, the method comprising:
   detecting a site loss condition associated with a site associated with the medical device based at least in part on measurement values for a physiological condition in a body of a user; and
   in response to detecting the site loss condition, providing, via a user interface, a user notification that indicates the site loss condition associated with the site.

2. The method of claim 1, wherein providing the user notification comprises indicating the user needs to change the site.

3. The method of claim 1, wherein providing the user notification comprises analyzing historical site location information to provide guidance.

4. The method of claim 1, further comprising calculating a frequency or a rate at which the site is utilized using historical data, wherein providing the user notification comprises providing guidance to change the site based at least in part on the frequency or the rate at which the site is utilized.

5. The method of claim 1, wherein providing the user notification comprises analyzing one or more of historic delivery data, measurement data and historical site location information to provide guidance as to a cause of the user notification.

6. The method of claim 1, further comprising determining a current value for a metric based on one or more of the measurement values, wherein detecting the site loss condition comprises detecting the site loss condition when a difference between the current value for the metric and a reference value for the metric is greater than a threshold.

7. The method of claim 1, further comprising averaging a subset of the measurement values during an initial period to obtain an average measurement value, wherein detecting the site loss condition comprises detecting the site loss condition when a difference between a current measurement value and the average measurement value is greater than a threshold.

8. The method of claim 1, wherein providing the user notification comprises providing one or more graphical user interface (GUI) notifications on a portable electronic device communicatively coupled to the medical device.

9. The method of claim 8, wherein the one or more GUI notifications comprise guidance influenced by a frequency or a rate at which the site is utilized.

10. A computer-readable medium having computer-executable instructions stored thereon that, when executed by a processor, cause the processor to:
    detect a site loss condition associated with a site associated with a medical device based at least in part on measurement values for a physiological condition in a body of a user; and
    provide a user notification that indicates the site loss condition associated with the site via a user interface in response to detecting the site loss condition.

11. The computer-readable medium of claim 10, wherein:
    the physiological condition comprises a glucose level;
    the measurement values include a current glucose measurement value; and
    the computer-executable instructions cause the processor to detect the site loss condition by:
        determining a current insulin estimate for achieving a reference glucose value based at least in part on the current glucose measurement value; and
        detect the site loss condition based on a relationship between the current insulin estimate and a reference insulin estimate.

12. The computer-readable medium of claim 11, wherein the computer-executable instructions cause the processor to:
    obtain, from a sensing arrangement, sensed glucose measurement values of the glucose level in the body of the user during fasting periods during an initial period;
    determine fasting amount of insulin in the body of the user during the fasting periods; and
    determine the reference insulin estimate for achieving the reference glucose value based at least in part on the fasting amount of insulin and the sensed glucose measurement values.

13. The computer-readable medium of claim 12, wherein the computer-executable instructions cause the processor to:
    determine a current amount of insulin in the body of the user; and
    determine the current insulin estimate for achieving the reference glucose value based at least in part on the current amount of insulin and the current glucose measurement value.

14. The computer-readable medium of claim 10, wherein the computer-executable instructions cause the processor to:
    calculate a frequency or a rate at which the site is utilized using historical data;
    provide guidance to change the site based at least in part on the frequency or the rate at which the site is utilized.

15. The computer-readable medium of claim 10, wherein the computer-executable instructions cause the processor to analyze one or more of historic delivery data, measurement data and historical site location information to provide guidance as to a cause of the user notification.

16. The computer-readable medium of claim 10, wherein the user notification comprises guidance to change the site based at least in part on a frequency or a rate at which the site is utilized.

17. The computer-readable medium of claim 10, wherein the computer-executable instructions cause the processor to provide the user notification as one or more graphical user interface (GUI) notifications on a portable electronic device communicatively coupled to the medical device.

18. The computer-readable medium of claim 17, wherein the one or more GUI notifications provide guidance based at least in part on a frequency or a rate at which the site is utilized.

19. An electronic device comprising:
    a user interface; and
    a control module coupled to the user interface, wherein the control module is configured to:
        detect a site loss condition associated with a site associated with a medical device based on one or more measurement values for a physiological condition in a body of a patient; and
        provide a graphical user interface (GUI) notification that indicates the site loss condition associated with the site via the user interface.

20. The electronic device of claim 19, wherein the control module is configured to:
    determine a reference value for a metric based on sensed measurement values for the physiological condition in the body of the patient during an initial period;

after the initial period:
  obtain an updated measurement value for the physiological condition in the body of the patient;
  determine a current value for the metric based at least in part on the updated measurement value; and
  detect the site loss condition based on a relationship between the current value for the metric and the reference value for the metric.

* * * * *